US009656940B2

(12) United States Patent
Amoros et al.

(10) Patent No.: US 9,656,940 B2
(45) Date of Patent: May 23, 2017

(54) PROCESS FOR THE RECOVERY OF ACETIC ACID

(75) Inventors: Daniel Amoros, Valleraugue (FR);
Mathias Brehelin, Lyons (FR);
Andreas Hummel, Freiburg (DE);
Thomas Krumrey, Teningen (DE)

(73) Assignee: SOLVAY ACETOW GmbH, Freiburg (DE)

( * ) Notice: Subject to any disclaimer, the term of this patent is extended or adjusted under 35 U.S.C. 154(b) by 122 days.

(21) Appl. No.: 14/118,083

(22) PCT Filed: May 14, 2012

(86) PCT No.: PCT/EP2012/058914
§ 371 (c)(1),
(2), (4) Date: May 8, 2014

(87) PCT Pub. No.: WO2012/156362
PCT Pub. Date: Nov. 22, 2012

(65) Prior Publication Data
US 2015/0051423 A1 Feb. 19, 2015

(30) Foreign Application Priority Data

May 17, 2011 (FR) .................................... 11 54265

(51) Int. Cl.
| | |
|---|---|
| *C07C 51/48* | (2006.01) |
| *C07C 51/44* | (2006.01) |
| *B01D 3/14* | (2006.01) |
| *B01D 3/40* | (2006.01) |
| *B01D 11/04* | (2006.01) |

(52) U.S. Cl.
CPC .............. *C07C 51/48* (2013.01); *B01D 3/141* (2013.01); *B01D 3/40* (2013.01); *B01D 11/043* (2013.01); *B01D 11/0446* (2013.01); *C07C 51/44* (2013.01)

(58) Field of Classification Search
CPC ......... C07C 53/08; C07C 51/44; C07C 51/48; B01D 11/043; B01D 11/0446; B01D 3/141; B01D 3/40
USPC ........................................................ 562/608
See application file for complete search history.

(56) References Cited

U.S. PATENT DOCUMENTS

| | | | |
|---|---|---|---|
| 6,793,777 B1 * | 9/2004 | Rudinger ................ | C07C 51/44 203/14 |
| 2009/0234157 A1 * | 9/2009 | Warner et al. ................ | 562/512 |

FOREIGN PATENT DOCUMENTS

WO    WO 03074781 A1    12/2003

OTHER PUBLICATIONS

Schultz ("Reduce Costs with Dividing-Wall Columns" CEP magazine (www.cepmagazine.org) May 2002, p. 64-71).*

(Continued)

*Primary Examiner* — Jafar Parsa
*Assistant Examiner* — Amy C Bonaparte
(74) *Attorney, Agent, or Firm* — Jarrod N. Raphael

(57) ABSTRACT

The present invention relates to a process for the recovery of acetic acid. The invention more particularly relates to a process comprising a stage of liquid/liquid extraction of an aqueous solution comprising acetic acid and to a stage of distillation of the extract obtained.

18 Claims, 3 Drawing Sheets

(56) References Cited

OTHER PUBLICATIONS

MTBE (Sigma-Aldrich Safety Data Sheet for tert-Butyl methyl ether p. 1-8, obtained Apr. 5, 2016).*

Long, Nguyen Van Duc, et al—"Design and optimization of a dividing wall column for debottlenecking of the acetic acid purification process", 2010, Chemical Engineering and Processing, Elsevier Sequoia, Lausanne, CH, vol. 49, No. 8, XP027234377, pp. 825-835; 11 pgs.

* cited by examiner

PROCESS FOR THE RECOVERY OF ACETIC ACID

RELATED APPLICATIONS

This application is a U.S. national stage entry under 35 U.S.C. §371 of International Application No. PCT/EP2012/058914, filed May 14, 2012, which claims priority to EP Application No. 11 54265 filed on May 17, 2011 The entire contents of these applications are hereby explicitly incorporated herein by this reference.

The present invention relates to a process for the recovery of acetic acid. The invention more particularly relates to a process comprising a stage of liquid/liquid extraction of an aqueous solution comprising acetic acid and to a stage of distillation of the extract obtained.

Acetic acid, acetic anhydride and peracetic acid are used in the organic chemistry industries, for example for the manufacture of cellulose acetate, alkyl acetates, ketenes, glycerol and epoxyalkanoic acids, and solutions comprising acetic acid are extracted from these processes.

For example, acetic acid is formed as byproduct at a concentration of 20% to 40% in the process for the manufacture of cellulose acetate, and acetic acid is formed as byproduct at a concentration of 10% to 15% in the process for the manufacture of glycerol by the use of peracetic acid. Aqueous solutions comprising acetic acid at such a mean concentration of between approximately 7% and approximately 40% are produced in large amounts as byproducts, and an efficient recovery of the acetic acid from these aqueous solutions is essential and important for improving the economic performance of the main processes. Moreover, acetic acid is used in other fields, for example in the metal-processing industries and in the fermentation industries, and aqueous solutions comprising acetic acid are also formed in these fields. In order to improve the degree of use of valued substances and to prevent environmental pollution, it is very important to recover the acetic acid from these aqueous solutions with high efficiency.

Methods for the recovery of acetic acid from aqueous solutions are known. One of these methods consists in carrying out a liquid/liquid extraction with a low-boiling-point solvent. Acetic acid is re-encountered in the solvent phase. The acetic acid, the solvent, a small amount of dissolved water and possibly high-boiling-point compounds, which make up the solvent phase, are then recovered, generally by distillation. This purification by distillation of numerous compounds can prove to be very complex and very expensive to carry out.

Furthermore, in the field of purification by distillation, dividing-wall and Petlyuk columns have been developed. These columns make it possible to limit the number of columns to be employed in the purification process, in comparison with a purification process with conventional columns, which simplifies the purification process and which ensures a reduction in the energy consumption.

A search is always under way for simple and relatively inexpensive processes for the recovery of acetic acid which make it possible to obtain compounds of high purity.

To this end, the invention provides a process for the recovery of acetic acid comprising a stage of liquid/liquid extraction of an aqueous solution comprising acetic acid with a low-boiling-point solvent, in order to extract the acid from the aqueous solution, and a stage of distillation of this extract, characterized in that the distillation is carried out in a dividing-wall column or in a Petlyuk column.

The aqueous solution comprising acetic acid introduced in the extraction stage of the invention advantageously comprises between 20% and 40% by weight of acetic acid. The acetic acid can result from a renewable material of animal or vegetable origin.

According to a specific embodiment of the process of the invention, this aqueous solution comprising acetic acid results from a process for the acetylation of wood pulp.

Generally, a process for the acetylation of wood pulp comprises the stages of bringing wood pulp into contact with acetic acid and of reacting with acetic anhydride in order to acetylate the cellulose. The product obtained is cellulose triacetate, which is subsequently hydrolyzed with water and a catalyst to form cellulose 2,5-acetate. An aqueous solution comprising between 20% and 40% by weight of acetic acid is recovered in the following section of precipitation and washing of the product with water.

According to this embodiment, the aqueous solution comprising acetic acid generally comprises high-boiling-point compounds. The process of the invention makes it possible to efficiently separate these compounds from the acetic acid. Mention may be made, as examples of high-boiling-point compounds, of sugars, salts, such as $NaHSO_4$ or $CaSO_4$, hemicelluloses, and the like.

According to this embodiment, the acetic acid recovered during the stage of distillation with a dividing-wall column or with a Petlyuk column, in at least one intermediate fraction, is recycled in the process for the acetylation of the wood. The acetic acid recovered in the intermediate fraction(s) can be in virtually pure form or in the form of a concentrated aqueous solution, for example comprising of the order of 60% by weight of acetic acid.

The process of the invention comprises a stage of liquid/liquid extraction of the aqueous solution comprising acetic acid with a low-boiling-point solvent, in order to extract the acid from the aqueous solution.

The low-boiling-point solvent has a lower boiling point than that of acetic acid.

The solvent is advantageously chosen from the group of the ethers, alcohols, acetates and ketones.

Preferably, the solvent is chosen from diethyl ether, methyl tert-butyl ether, isopropyl alcohol, isopropyl acetate, ethyl acetate, methyl acetate and methyl ethyl ketone.

The extraction stage can be carried out in numerous devices in which two liquid phases are brought into contact with one another. For efficient extraction, it is preferable to choose a device in which the interface between the two liquid phases is frequently "refreshed". In the chemical industry, use is generally made, as continuous extraction devices, of columns having stacked packing or random packing, or perforated plate columns. It is also possible to use a cascade of mixers/decanters.

Stirred column extraction devices, such as disk/ring columns of RDC (rotary disk contactor) type or stirred columns of Oldshue-Rushton type, can be used in order to improve the mixing between the solvent and aqueous phases.

Preferably, contact between the solution comprising acetic acid to be extracted and the low-boiling-point solvent is carried out countercurrentwise.

Advantageously, the temperature during the extraction stage is less than or equal to 50° C. The pressure during this stage is preferably atmospheric pressure.

The solvent phase resulting from the extraction (extract) mainly comprises acetic acid and solvent, a small amount of dissolved water and possibly high-boiling-point compounds.

The process of the invention also comprises a stage of distillation, in a dividing-wall column or in a Petlyuk column, of the extract resulting from the extraction stage.

The aim of this distillation in a dividing-wall column or in a Petlyuk column is the efficient separation and recovery of the various compounds of the extract, namely the extraction solvent, the acetic acid and possibly the high-boiling-point compounds.

The following are generally recovered:
- at the column top, the extraction solvent and possibly a small amount of water,
- in the side part of the column, at least one intermediate fraction; the intermediate fraction(s) comprise(s) acetic acid in virtually pure form or acetic acid in the form of a concentrated aqueous solution,
- at the column bottom, high-boiling-point compounds, alone or as a mixture with acetic acid.

The term "dividing-wall column" is understood to mean a column, a portion of the column of which is separated vertically into two parts by a dividing wall. The presence of the dividing wall generates a prefractionating section located in the feed region.

The Petlyuk column is an alternative to the dividing-wall column. It is a column in which the prefractionating section of the dividing-wall column is replaced with a separate prefractionating column, the top product from which is introduced into the top part of the following column (which is not a dividing-wall column) and the bottom product from which is introduced into the bottom part of this column. The prefractionating column does not have a boiler or condenser, with a dividing wall, but liquid from the top part of the column following the prefractionating column and vapor from the bottom part of this following column are introduced into the prefractionating column.

The dividing-wall column of the invention comprises at least one dividing wall. Preferably, it comprises just one dividing wall.

The dividing wall can be a metal plate welded to the column, which can, for example, have a thickness of approximately 1.5 mm. It can also be a dividing wall not welded to the shell and integral with the internal parts of the column.

The dividing wall is preferably located in the middle of the column, on either side of the point where the feed stream is introduced into the column and on either side of the point where the intermediate fraction(s) is(are) recovered.

The dimensions of the dividing-wall column can be highly variable. Its diameter can, for example, vary between 0.3 and more than 5 m. Its height can range up to 100 m.

Advantageously, the pressure of the column is atmospheric pressure.

Preferably, the temperature range between the column top and the column bottom is between 20 and 130° C.

The intermediate fraction(s) recovered advantageously comprise(s) between 50% and 100% by weight of acetic acid.

Advantageously, the extraction solvent recovered at the column top, during the distillation, is recycled in the extraction stage. At the column top, the extraction solvent can comprise a small amount of water; it can, for example, comprise between 0% and 10% by weight of water. Also, before being recycled in the extraction stage, the water can be separated from the solvent, for example by simple separation by settling.

The process of the invention, comprising an extraction stage and a distillation stage with a dividing-wall column or a Petlyuk column, makes it possible to recover the acetic acid and the extraction solvent with a high purity. The process is simple and highly advantageous economically. By using a dividing-wall column or a Petlyuk column, it is possible to reduce the number of columns (and thus to reduce the number of column casings, boilers, condensers or internal parts), which considerably reduces the capital costs of the distillation plant and its complexity. It also makes possible a significant reduction in the energy consumption.

Other details or advantages of the invention will become more clearly apparent in the light of the examples given below.

EXAMPLES

Example 1 (Comparative)

Figure 1:
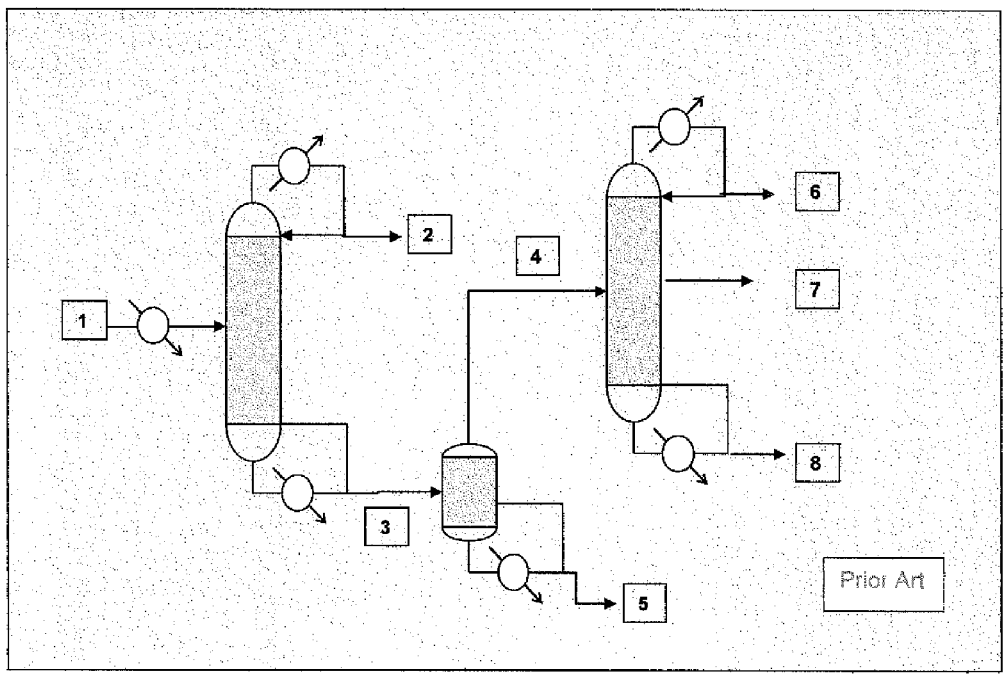
FIG. 1 represents the diagram of a conventional process for the recovery of acetic acid.

FIG. 1 represents the diagram of a conventional process for the recovery of acetic acid.

On conclusion of the process for the acetylation of cellulose, the stage of extraction of an aqueous acetic acid solution comprising 30% by weight of acetic acid is carried out. The extraction solvent is diethyl ether. The extraction is carried out at 25° C. and at atmospheric pressure in a perforated plate column.

The stream 1 represents the product extracted by the solvent originating from the extraction stage. The stream 1 is composed of a mixture of water, solvent, acetic acid and high-boiling-point compounds. The stream 1 is introduced into a distillation column. The stream 2 is the distillate exiting at the column top; it is composed predominantly of solvent, which is recycled in the extraction stage. The stream 3 exiting at the bottom of the column is introduced into a flash drum. This flash separates the stream 3 into 2 other streams: the stream 4, comprising a mixture of water and acetic acid with a proportion of acetic acid of 75% by weight, and the stream 5, comprising the majority of the high-boiling-point compounds. The stream 4 feeds the column for the purification of acetic acid. At the column top, a water-rich mixture 6, comprising from 70% to 90% by weight of water, is extracted and returned to the extraction stage. The stream 7, composed of a mixture of water and acetic acid in a proportion of water ranging from 35% to 45%, is withdrawn on the side part of this column; this stream is recycled to the process for the acetylation of cellulose. The stream 8, which is withdrawn in the column bottom, is pure (99.5%) acetic acid, which is recycled to the process for the acetylation of cellulose.

Example 2

Figure 2:
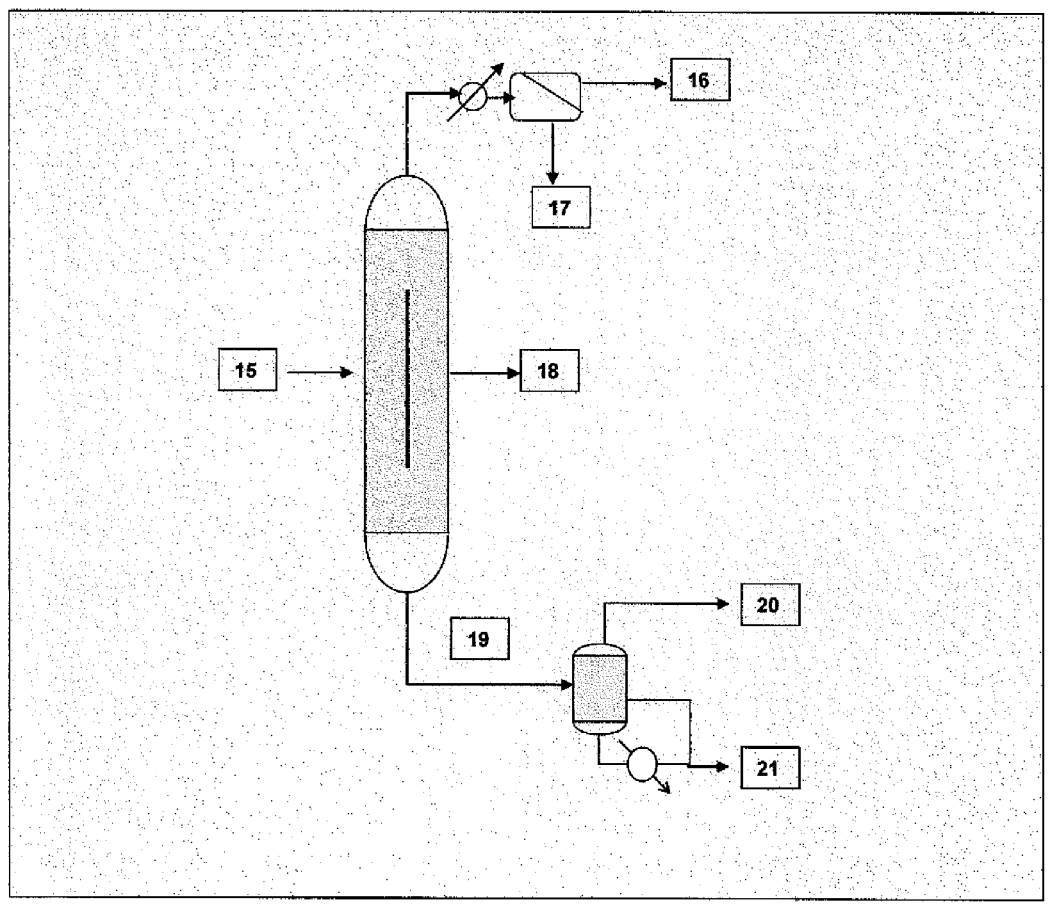
FIG. 2 represents the diagram of an embodiment of the process of the invention.

FIG. 2 represents the diagram of an embodiment of the process of the invention comprising a dividing-wall column and a flash drum.

The stream 15 represents the product extracted by the solvent originating from the extraction stage (same conditions for the extraction stage as for comparative example 1). The stream 15 is introduced into a dividing-wall column. The streams 16 and 17 result from a separation by settling, at a temperature of between 5 and 40° C. and preferably 20° C., of the stream exiting at the dividing-wall column top. The stream 16 predominantly comprises the solvent, which is recycled to the extraction stage, and the stream 17 predominantly comprises water. The stream 18 is withdrawn in the region occupied by the dividing wall opposite the stream 15 and is composed of a mixture of acetic acid and water comprising between 50% and 70% by weight of acetic acid. This stream 18 is recycled to the reaction section of the process for the acetylation of cellulose. The stream 19 is extracted at the dividing-wall column bottom and comprises acetic acid and high-boiling-point compounds. This stream feeds a flash drum. This flash separates the stream 19 into 2 other streams: the stream 20, comprising pure acetic acid, which is recycled to the reaction section of the process for the acetylation of cellulose, and the stream 21, comprising high-boiling-point compounds and acetic acid. An example of the implementation of the process according to this embodiment is described below.

The compositions of the various streams and also the operating conditions are described in table 1 below. The percentages mentioned in the table are percentages by weight.

TABLE 1

| | Stream | | | | | | |
|---|---|---|---|---|---|---|---|
| | 15 | 18 | 19 | 21 | 20 | 16 | 17 |
| Acetic acid (%) | 15.82 | 57.65 | 98.76 | 49.98 | 99.92 | 0.12 | 0.33 |
| Water (%) | 6.91 | 42.35 | 0.08 | 0.02 | 0.08 | 1.08 | 95.63 |
| Solvent (%) | 77.14 | — | — | — | — | 98.80 | 4.04 |
| High-boiling-point compounds (%) | 0.13 | — | 1.16 | 50.00 | — | — | — |
| Throughput (kg/h) | 38751.6 | 3200.0 | 4300.0 | 100.0 | 4200 | 30211.4 | 1040.2 |
| Temperature (° C.) | 50 | 102 | 118 | 118 | 118 | 25 | 25 |

The distillation region located above the region occupied by the dividing wall has an efficiency corresponding to 12 theoretical stages.

The distillation region located below the region occupied by the dividing wall where the side stream 18 is withdrawn has an efficiency corresponding to 15 theoretical stages.

The distillation region located in the left-hand part of the region occupied by the dividing wall where the feeding of the column with the stream 15 is carried out has an efficiency corresponding to 12 theoretical stages.

The distillation region located in the right-hand part of the region occupied by the dividing wall where the side stream 18 is withdrawn has an efficiency corresponding to 8 theoretical stages.

The column is operated at atmospheric pressure and the reflux ratio at the column top is 1.

The dividing-wall column device makes it possible to separate, with just one apparatus: the solvent, which is recycled to the extraction stage, a mixture of acetic acid and water, which is recycled to the process for the acetylation of cellulose, pure acetic acid comprising high-boiling-point compounds which are to be separated in a flash drum.

Example 3

Figure 3:
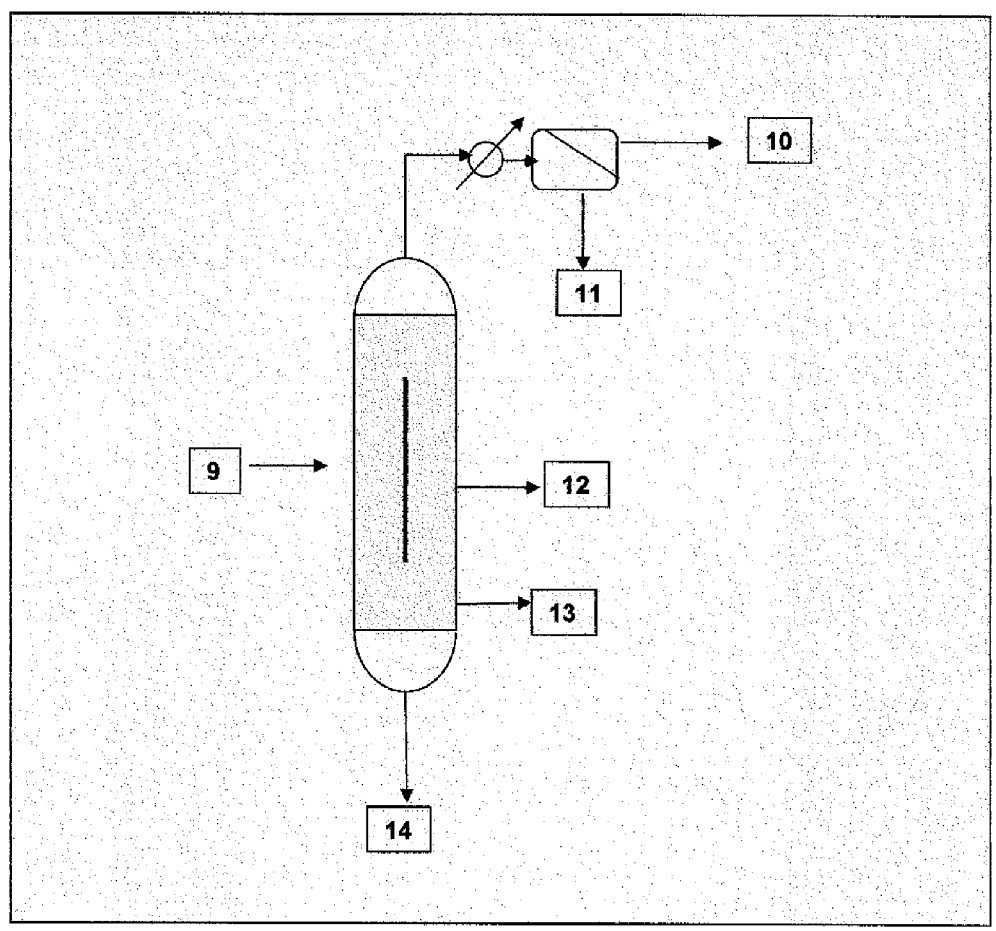
FIG. 3 represents the diagram of another embodiment of the process of the invention.

FIG. 3 represents the diagram of an embodiment of the process of the invention comprising a dividing-wall column.

The stream 9 represents the product extracted by the solvent originating from the extraction stage (same conditions for the extraction stage as for comparative example 1). It is composed of a mixture of water, solvent, acetic acid and high-boiling-point compounds. The stream 9 is introduced into the dividing-wall column. The column top stream has a temperature of between 30 and 35° C. and is composed of a mixture of water and solvent comprising approximately 4% by weight of water. This stream feeds a decanter, which has a temperature of between 5 and 40° C. and preferably 20° C. The streams 10 and 11 result from this separation by settling. The stream 10 predominantly comprises the solvent, which is recycled to the extraction stage, and the stream 11 predominantly comprises water. The stream 12 is withdrawn in the region occupied by the dividing wall opposite the stream 9 and is composed of a mixture of acetic acid and water comprising between 50% and 70% by weight of acetic acid. This stream 12 is recycled to the reaction section of the process for the acetylation of cellulose. The stream 13 is withdrawn below the region occupied by the dividing wall of the column and is composed of pure acetic acid. This stream 13 is recycled to the reaction section of the process for the acetylation of cellulose. The stream 14 is withdrawn at the bottom of the dividing-wall column and comprises high-boiling-point compounds and acetic acid.

An example of the implementation of the process according to this embodiment is described below.

The compositions of the various streams and also the operating conditions are described in table 2 below. The percentages mentioned in the table are percentages by weight.

TABLE 2

| | Stream | | | | | |
|---|---|---|---|---|---|---|
| | 9 | 12 | 13 | 14 | 10 | 11 |
| Acetic acid (%) | 15.82 | 57.65 | 99.92 | 49.98 | 0.12 | 0.33 |
| Water (%) | 6.91 | 42.35 | 0.08 | 0.02 | 1.08 | 95.63 |
| Solvent (%) | 77.14 | — | — | — | 98.80 | 4.04 |
| High-boiling-point compounds (%) | 0.13 | — | — | 50.00 | — | — |
| Throughput (kg/h) | 38751.6 | 3200.0 | 4200.0 | 100.0 | 30211.4 | 1040.2 |
| Temperature (° C.) | 50 | 102 | 118 | 118 | 25 | 25 |

The distillation region located above the region occupied by the dividing wall has an efficiency corresponding to 12 theoretical stages.

The distillation region located below the region occupied by the dividing wall where the side stream 13 is withdrawn has an efficiency corresponding to 15 theoretical stages.

The distillation region located in the left-hand part of the region occupied by the dividing wall where the feeding of the column with the stream 9 is carried out has an efficiency corresponding to 12 theoretical stages.

The distillation region located in the right-hand part of the region occupied by the dividing wall where the side stream 12 is withdrawn has an efficiency corresponding to 8 theoretical stages.

The column is operated at atmospheric pressure and the reflux ratio at the column top is 1.

The dividing-wall column device makes it possible to separate, with just one apparatus: the solvent, which is recycled to the extraction stage, a mixture of acetic acid and water, which is recycled to the process for the acetylation of cellulose, pure acetic acid, which is also recycled to the process for the acetylation of cellulose, and high-boiling-point compounds, which are destroyed.

The invention claimed is:

1. A process for the recovery of acetic acid, comprising:
   extracting acetic acid from an aqueous solution by liquid/liquid extraction of the aqueous solution with a low-boiling-point solvent to form an extract, the low-boiling-point solvent having a boiling point lower than acetic acid, and the extract comprises at least acetic acid, the low-boiling-point solvent, water, and high-boiling-point compounds; and
   distilling the extract from the extracting step in a dividing-wall column or in a Petlyuk column to obtain:
   (i) a top product comprising the low-boiling-point solvent and optionally water;
   (ii) at least one intermediate fraction comprising from 50% to 100% by weight of acetic acid and optionally water; and
   (iii) a bottom product comprising high-boiling compounds or a mixture of high-boiling compounds and acetic acid.

2. The process as claimed in claim 1, wherein the aqueous solution comprises between 20% and 40% by weight of acetic acid.

3. The process as claimed in claim 1, wherein the aqueous solution results from a process for the acetylation of wood pulp.

4. The process as claimed in claim 3, wherein acetic acid recovered, in at least one intermediate fraction, by distilling the extract is recycled in the process for the acetylation of wood pulp.

5. The process as claimed in claim 1, wherein the low-boiling-point solvent is selected from the group consisting of the ethers, alcohols, acetates, and ketones.

6. The process as claimed in claim 5, wherein the low-boiling-point solvent is selected from the group consisting of diethyl ether, methyl tert-butyl ether, isopropyl alcohol, isopropyl acetate, ethyl acetate, methyl acetate and methyl ethyl ketone.

7. The process as claimed in claim 1, wherein the pressure of the column is atmospheric pressure.

8. The process as claimed in claim 1, wherein the temperature range within the column between the top of the column and the bottom of the column is between 20° C. and 130° C.

9. The process as claimed in claim 1, wherein the low-boiling-point solvent is recovered after distillation of the extract by settling of a solvent/water mixture exiting at the column top.

10. The process as claimed in claim 9, wherein the low-boiling-point solvent is recycled in the extraction stage.

11. A process for the recovering and recycling of acetic acid, comprising:
    extracting acetic acid from an aqueous solution that comprises between 20% and 40% by weight of acetic acid by liquid/liquid extraction of the aqueous solution with a low-boiling-point solvent having a boiling point less than the boiling point of acetic acid and selected from ethers, alcohols, acetates, and ketones, and
    distilling low-boiling-point solvent extract from the extracting step in a dividing-wall distillation column or in a Petlyuk distillation column to obtain:
    (i) a top product comprising low-boiling-point solvent and from 0% to 10% by weight water,
    (ii) at least one intermediate fraction comprising from 50% to 100% by weight of acetic acid and optionally water, and
    (iii) a bottom product comprising high-boiling compounds or a mixture of high-boiling compounds and acetic acid,
    recovering low-boiling-point solvent from the top product,
    recycling recovered low-boiling-point solvent in the step of extracting, and
    recycling the at least one intermediate fraction in a process for the acetylation of wood pulp.

12. The process of claim 11, wherein the bottom product comprises a mixture of high-boiling compounds and acetic acid and the process further comprises:
    recovering acetic acid from the bottom product, and
    recycling acetic acid recovered from the bottom product in the process for the acetylation of wood pulp.

13. The process of claim 1, wherein the extracted acetic acid has a purity of about 99% or greater.

14. The process of claim 11, wherein the low-boiling-point solvent extract comprises at least acetic acid, the low-boiling-point solvent, water, and high-boiling-point compounds.

15. The process of claim 1, wherein the extract comprises more of the low-boiling-point solvent than the acetic acid.

16. The process of claim 11, wherein the low-boiling-point solvent extract comprises more of the low-boiling-point solvent than the acetic acid.

17. The process of claim 1, wherein the extract comprises less than 16 wt. % of the acetic acid prior to distilling in the dividing-wall column or the Petlyuk column.

18. The process of claim 11, wherein the low-boiling-point solvent extract comprises less than 16 wt. % of the acetic acid prior to distilling in the dividing-wall distillation column or the Petlyuk distillation column.

* * * * *